(12) United States Patent
Gallegos et al.

(10) Patent No.: US 7,349,806 B2
(45) Date of Patent: Mar. 25, 2008

(54) SYSTEM AND METHOD FOR EXTRACTING OPTICAL PROPERTIES FROM ENVIRONMENTAL PARAMETERS IN WATER

(75) Inventors: Sonia C Gallegos, Slidell, LA (US); Juanita C Sandidge, Diamondhead, MS (US); Xiaogang Chen, Slidell, LA (US); Cynthia D Daniels, Gulfport, MS (US); Chiu-Fu Cheng, Picayune, MS (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/229,435

(22) Filed: Sep. 15, 2005

(65) Prior Publication Data
US 2006/0235616 A1  Oct. 19, 2006

Related U.S. Application Data (60) Provisional application No. 60/610,862, filed on Sep. 15, 2004.

(51) Int. Cl.
G06F 19/00 (2006.01)
(52) U.S. Cl. .............................. 702/5; 702/3
(58) Field of Classification Search ................ 702/2, 702/3, 4, 5
See application file for complete search history.

(56) References Cited

U.S. PATENT DOCUMENTS

| | | | | |
|---|---|---|---|---|
| 5,243,541 A | * | 9/1993 | Ulich | 348/81 |
| 5,504,714 A | * | 4/1996 | Shonting | 367/13 |
| 6,775,617 B2 | * | 8/2004 | Seemann et al. | 702/3 |
| 6,873,716 B1 | * | 3/2005 | Bowker et al. | 382/128 |
| 7,057,199 B2 | * | 6/2006 | Perry | 250/577 |
| 7,120,089 B1 | * | 10/2006 | Shonting et al. | 367/131 |

OTHER PUBLICATIONS

J.E. Moon, Y.H. Ahn, J.H.RYU, J.K. Choi, "Study on the seasonal variation for oceanic environment of Yellow Sea coastal area using ferry ship and satellite data", IEEE International Geoscience and Remote Sensing Symposium, p. 2515-2518, Jul. 2005.

"Webcast with Dr. Sonia Gallegos", [online], [retrieved on Mar. 22, 2004], retrieved from the internet <URL: http://cerser.ecsu.edu/03events/030403go/sgwebcast.html>.

"NRL7320:Yellow and East China Seas Response to Winds and Currents Project", [online], [retrieved on Mar. 22, 2004], retrieved from the internet <URL: http://www7320.nrlssc.navy.mil/html/yes-home.html>.

(Continued)

*Primary Examiner*—Donald E McElheny, Jr.
(74) *Attorney, Agent, or Firm*—John J. Karasek; Sally A. Ferrett (57) ABSTRACT

A method for predicting water clarity at a plurality of water depths for a location including providing training data to a neural network, the training data representative of water measurements at the location, thereafter receiving inputs including temperature, salinity, tidal information, water depth, and sediment data, and generating values for optical attenuation at a wavelength at a plurality of depths. In one embodiment, a default cloudy day algorithm operates at all times and a clear sky algorithm operates only when clear satellite images are available.

20 Claims, 7 Drawing Sheets

OTHER PUBLICATIONS

"NRL7320:Yellow and East China Seas Satellite Remote Sensing", [online], [retrieved on Mar. 22, 2004], retrieved from the internet <URL: http://www7320.nrlssc.navy.mil/html/yes-gregg.html>.

"NRL7320:Yellow and East China Seas Insutu Measurements", [online], [retrieved on Mar. 22, 2004], retrieved from the internet <URL: http://www.7320.nrlssc.navy.mil/html/yes-bill.html>.

"NRL7320:Yellow and East China Seas Numerical Ocean Modeling", [online], [retrieved on Mar. 22, 2004], retrieved from the internet <URL: http://www7320.nrlssc.navy.mil/html/yes-shelley.html>.

Haltrin, V. I. and Gallegos, S. C., "About Nonlinear Dependence of Remote Sensing and Diffuse Reflection Coefficients on Gordon's Parameter," Proceedings of the II International Conference "Current Problems in the Optics of Natural Waters" St. Petersburg, Russia on Sep. 8-12, 2003, edited by Levin, I. and Gilbert, G., pp. 363-369.

S.C. Gallegos and J. Sandidge, "Summary of Observations and Modeling of Optical Properties in the Yellow Sea", Eos. Trans. AGU, 83(4), Ocean Sciences Meet. Suppl., Abstract OS22N-10, 2002, 2 pages.

Gallegos, S.C., Holyer, R.J., Sandidge, J., Pistek, P, Hahn, S.D., Jeong, H., and Ahn, Y., "An Optical Backscattering Algorithm for the Yellow Sea", Proceedings of the Fourth Pacific Ocean Remote Sensing Conference, Quingdao, China, on Jul. 28-31, 1998, vol. 2, pp. 1-6.

Y.H. Ahn, J.E. Moon, and S. Gallegos, "Development of Suspended Particulate Matter Algorithms for Ocean Color Remote Sensing", Proceedings of the Autumn Meeting of the Korean Society of Oceanography, Oct. 2003, 17 pages.

Y.H. Ahn, J.E. Moon, and S. Gallegos, "Development of Suspended Particulate Matter Algorithms for Ocean Color Remote Sensing", Korean Journal of Remote Sensing, vol. 17, No. 4, pp. 285-295, Dec. 2001.

Ahn, Y., Shanmugam, P., and Gallegos, S., "Evolution of Suspended Sediment Patterns in the East China and Yellow Seas," Proceedings of the Yellow Sea International Symposium, Ansan, Korea, conference date Nov. 6-7, 2003, pp. 215-229, and in Journal of the Korean Society of Oceanography, vol. 39, Issue 1, pp. 26-34, Mar. 2004.

Gallegos, S. C., Sandidge, J., Chen, X., Hahn, S. D., Cho, S., Jeong, H. D., Suh, Y. S., and Ahn, Y., "Measuring and Modeling the Spectral Attenuation of Light in the Yellow Sea," Proceedings of Yellow Sea International Symposium, Anson, Korea, pp. 199-214, conference date Nov. 6-7, 2003, and in Journal of the Korean Society of Oceanography, vol. 39, Issue 1, pp. 46-56, Mar. 2004.

Ahn, Y., Shanmugam, P., and Gallegos, S., "Particle size distribution and optical properties of suspended sediment matter in the coastal oceans of Korea," in Proceedings of the Autumn Meeting, 2003 of the Korean Society of Oceanography in Pusan, Korea on Nov. 6-7, 2003, pp. 66-73.

* cited by examiner

| DEPTH (m) | TRAINING SET 36 CTD28 | CTD29 | TRAINING SET 62 CTD28 | CTD29 | TRAINING SET 108 CTD28 | CTD29 | TRAINING SET 173 CTD28 | CTD29 |
|---|---|---|---|---|---|---|---|---|
| 5 | 5.73 | 1.28 | 2.62 | 1.94 | 0.86 | 2.01 | 0.56 | NA |
| 15 | 5.00 | 0.93 | 2.53 | 1.22 | 1.08 | 1.53 | 0.65 | NA |
| 25 | 4.38 | 0.92 | 2.39 | 1.11 | 1.28 | 1.39 | 0.80 | NA |
| 35 | 2.07 | 1.13 | 2.29 | 0.97 | 1.76 | 1.07 | 0.69 | NA |
| 45 | 1.09 | 1.54 | 1.73 | 1.14 | 0.95 | 1.04 | 0.71 | NA |
| 55 | 0.93 | 1.41 | 1.17 | 2.16 | 0.87 | 1.19 | 0.73 | NA |

SYSTEM AND METHOD FOR EXTRACTING OPTICAL PROPERTIES FROM ENVIRONMENTAL PARAMETERS IN WATER

CROSS-REFERENCE TO RELATED APPLICATIONS

This Application is a Non-Prov of Prov (35 USC 119(e)) application 60/610,862 filed on Sep. 15, 2004.

BACKGROUND OF THE INVENTION

In ocean applications, is often useful to be able to predict spectral attenuation of light and visibility at different ocean depths. Satellite measurements can be used, however, are of limited use for predicting future values at different times of day and in different seasons.

Dynamic climatology models have been developed by the Naval Research Laboratory that provide daily surface estimates for a 365 day period of diffuse attenuation coefficient $K(\lambda)$ extracted from seven years of imagery collected by the Coastal Zone Color Scanner. The composites were of limited use due spectral restriction to 8 bits, a limited regional coverage, and restriction to surface estimates only.

BRIEF SUMMARY OF THE INVENTION

One embodiment of the invention is directed to a method for predicting water clarity at a plurality of water depths for a location. The method includes providing training data to a neural network, the training data representative of water measurements at the location, thereafter receiving inputs including temperature, salinity, tidal information, water depth, and sediment data, and generating values for optical attenuation at a wavelength at a plurality of depths.

The wavelength is 532 nanometers in one embodiment. The tidal information can be sea surface height and current velocity. The training data can include include measurements of water clarity, and irradiance measurements from at least one satellite. The training data can be a set of data from a plurality of locations.

The method can include generating values for visibility at at least one depth at the location. The method can include generating values for visibility at the plurality of depths at the location.

The method can include receiving irradiance data from a satellite, and incorporating said irradiance data in said generating of said values of optical attenuation. The method can include generating a first set of values of optical attenuation using a first algorithm that does not receive irradiance data from the satellite, and generating a second set of values of optical attenuation using a second algorithm that does receive irradiance data from the satellite. The second set of values of optical attenuation can be done only when cloud-free satellite images are available. The first and second algorithms use a gradient descent search to minimize mean squared error between desired output patterns and an output value of the neural network.

In an exemplary embodiment, the training data are input to the first algorithm, and both the first and second algorithms are updated with results of training the first algorithm.

The plurality of depths can extend from a water surface to an ocean bottom. The plurality of depths can extend to about 60 meters below a water surface. The plurality of depths can be between two and three meters apart.

The method can include generating values at a plurality of locations within a grid. The grid can have a resolution of about 0.5 degrees. In an embodiment, the method can include generating a map representation of the grid with said values shown on said map representation.

DETAILED DESCRIPTION OF THE INVENTION

Figure 1:
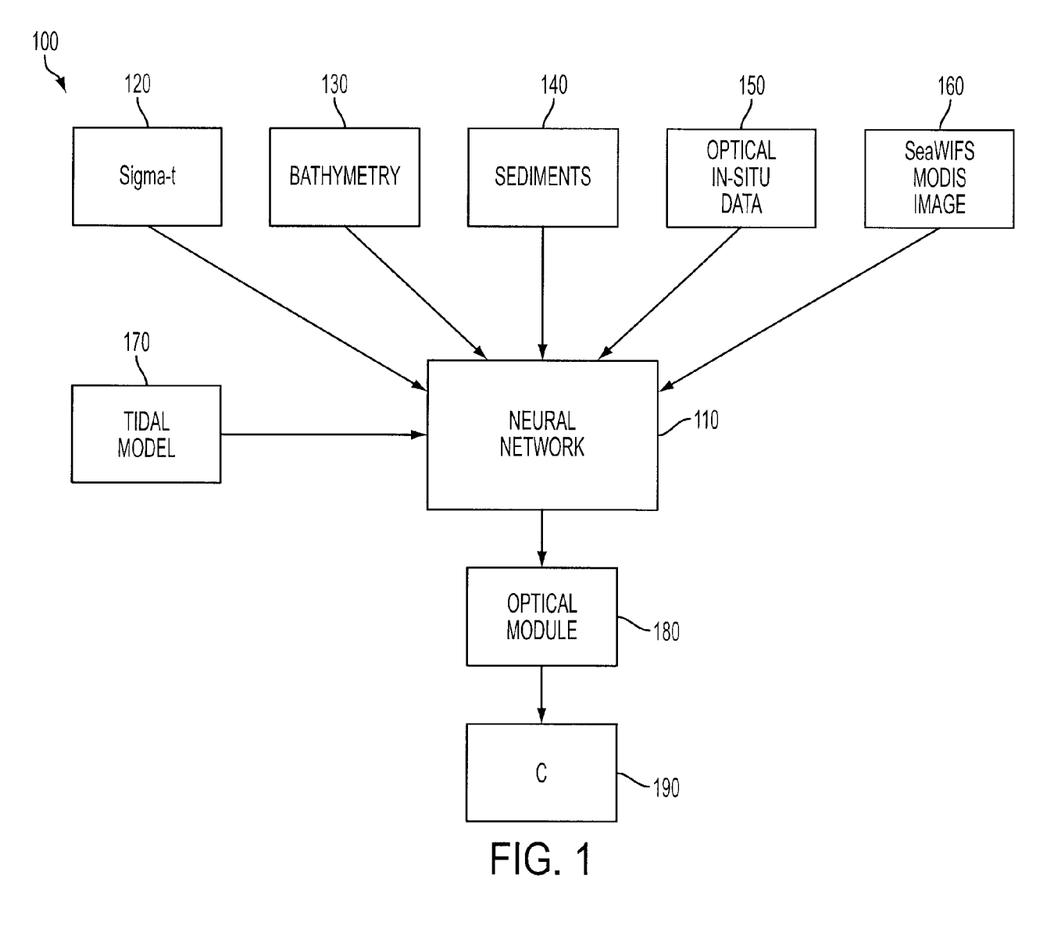
FIG. 1 is a schematic view of a system for predicting water clarity and visibility with respect to depth in accordance with an embodiment of the invention.

FIG. 1 is a schematic illustration of a system 100 and method for predicting water clarity in terms of a spectral attenuation coefficient ($K(\lambda)$) and visibility with respect to depth over a prediction region. The system is particularly useful for coastal areas where the depth is less than about 60 m, tidal regions where sediment levels can be high, and in regions that have frequent cloud cover over an annual period, although it is suitable for use in any region. In particular, the model is useful for coastal and murky shallow water. A grid at a desired grid resolution is overlaid over the prediction region, and predictions are generated at each grid point and depth.

A neural network 110 receives data during a training phase for a particular prediction region. After the training phase is complete, the neural network is operational and can operate without input of additional data. The network 110 has a model that includes a clear sky algorithm for use when satellite data is available and a default (cloudy sky) algorithm for use when satellite data is not available. In an exemplary embodiment, the clear sky algorithm and the default algorithm are set to run at all times, with the clear sky algorithm producing results only when satellite data is available and provided to the system.

The neural network 110 receives density data 120, bathymetry data 130 (depth), and measured sediment data 140, optical in-situ data 150, current speed and direction from a tidal model 170, and optionally, satellite data 160 when available.

The tidal model 170 that provides tidal coefficient inputs for the neural network 110 uses an adjoint approach to data assimilation in coastal waters based on the shallow water equations of motion. Discussion of an adjoint approach is found in D. A. Griffin, and K. R. Thompson, "The adjoint method of data assimilation used operationally for shelf circulation", J. Geophysical Research, Vol. 98, pages 8505-

8516, 1998. The tidal model 170 assimilates frequencies of the four dominant tidal components, M2, S2, N2, and K1 from tidal stations located along the coast of the prediction region. In an exemplary embodiment, the tidal model 170 produces estimations of sea surface height (SSH) and tidal current velocity (speed and direction) at 10-km intervals throughout the tidal cycle. To produce tidal inputs, the tidal information is interpolated at 5-km intervals.

Density of seawater is a function of temperature and salinity of the seawater. The density parameter 120 for use in the training mode of the neural network is a result of in situ measurements of temperature and salinity obtained simultaneously with the optics measurements in the prediction region.

In an exemplary embodiment, the density parameter for the neural network in an operational mode is computed from temperature and salinity outputs of the Modular Ocean Data Assimilation System (MODAS), and provides as input to the network three-dimensional grids of temperature and salinity. The MODAS system combines observed ocean data with climatological information to produce quality controlled grided estimates, and can assimilate remotely acquired SSH from satellites such as TOPEX/ERS-2, sea surface temperature from NOAA-n AVHRR and local expendable bathymeters (XBTs) data to produce near-real time estimations worldwide. The MODAS system can provide $\sigma_t$ density at 13 depths once per day, although other depth increments and frequency are also possible. In shallow areas (<150 m), such as the Yellow Sea, MODAS generally does not incorporate remotely acquired SSH from satellites. Additional information regarding the MODAS tidal model is found in Fox, D. N., W. J. Teague, C. N. Barron, M. R. Carnes, and C. M. Lee, "The Modular Ocean Data Assimilation System (MODAS)", Journal of Atmospheric and Oceanic Technology, Vol. 19, pages 240-252, 2002. The system 100 can use other models and systems for inputting density information to the neural network.

Data representative of density can provided to the network either as temperature and salinity from which density can be derived, or as a derived density value.

The bathymetry data 130 that is an input to the neural network is a set of water depth at grid points for a grid over the prediction region. Any suitable bathymetry database can be used, for example, a 1-minute resolution data set available from the Laboratory for Coastal and Ocean Dynamic Studies of Sun Kyun Kwan University (SKKU) in Korea (Choi, 1999), re-sampled to match the grid resolution for the neural network, for example, to a 0.05° resolution. Alternately, any other suitable bathymetry database can be input to the neural network, for example, the DBDB2Navy bathymetry databases.

Sediment information 140 can be provided from any suitable source for the prediction region, for example, from sediment type charts in the form of a contoured sediment map. The sediment type information can be derived from cruise data and literature searches, as well as from bottom samples.

The satellite data 160 that is an optional input to the model is the water leaving radiance $L_w$ at the 532 nm wavelength (or alternatively, at a different wavelength) obtained from satellite remote sensors such as MODIS or SeaWIFS. This data is available only in sunlight hours and when cloud free satellite images are available.

The training data is a set of data collected over different seasons. Input during the training phase includes in situ optical measurements of spectral light attenuation and oceanographic parameters of current speed and direction, sea water density, sediment type and bathymetry.

The neural network 110 uses a gradient search technique to minimize the mean squared error between the desired output patterns and the neural network value.

In an exemplary embodiment, the neural network includes a network layer, a hidden layer, and an output layer with one node. Initial weights are randomly chosen then mathematically adjusted on subsequent iterations, with evaluation of the performance of the weighted inputs in relation to the desired output pattern being done with a hyperbolic tangent function.

The three dimensional grid can have depth layers that are 2-3 meters in depth each, or greater or lesser, and a horizontal grid of 0.5 degrees, or greater or lesser.

In an exemplary embodiment, the cloudy sky algorithm can include an input layer of 28 nodes, a hidden layer, and an output layer with one node. The clear sky algorithm includes the 28 nodes of the default cloudy sky algorithm, a hidden layer, and an output layer with one node, plus an additional input node for the satellite data. The number of nodes refers to the number of inputs to the model. The input to the clear sky algorithm that is not an input to the default algorithm is the normalized water leaving irradiance, $L_w n$, at 532 nm wavelength. The normalized water leaving irradiance is a normalized value based on in situ measurements and satellite measurements. The normalized water leaving irradiance is an input to the model in both a training mode and an operational mode.

Satellite data is preferably input to the system for prediction times within one hour before and one hour after the time of the satellite acquisition. Extrapolating the satellite data to periods outside this two hour window is possible, however, may result in errors as high as 200%.

The default algorithm operates at all times, and the clear sky algorithm operates only when cloud free satellite measurements are available, so the default algorithm produces results at all times and the clear sky algorithm produces results only when satellite imagery is available. Depending on the amount of cloud cover for a given region, the clear sky algorithm can operate 10-15 or more percent of the time.

Estimates of swimmer's visibility with respect to depth are determined simultaneously with the spectral attenuation coefficients using a Preisendorfer visibility equation sw=4/$x_i$, where sw is the estimated swimmer's visibility and $x_i$ is the estimated attenuation coefficient. Each time the model is run, the model generates two cubes of data, including one cube of data containing the attenuation coefficient outputs and another cube of data containing the swimmer's visibility outputs.

In particular, the system produces as an output maps of spectral attenuation coefficients and swimmer's visibility at a particular wavelength at user defined depth intervals from the water surface to the ocean bottom. The wavelength can be 532 nm, for example. In an exemplary embodiment, the system produces results from the surface to a maximum depth of 60 meters. Results can be extrapolated to depths beyond the 60 meter depth if desired. It is noted that results are better if not extrapolated beyond the depths for which training data sets have been included in the model.

Figure 2:
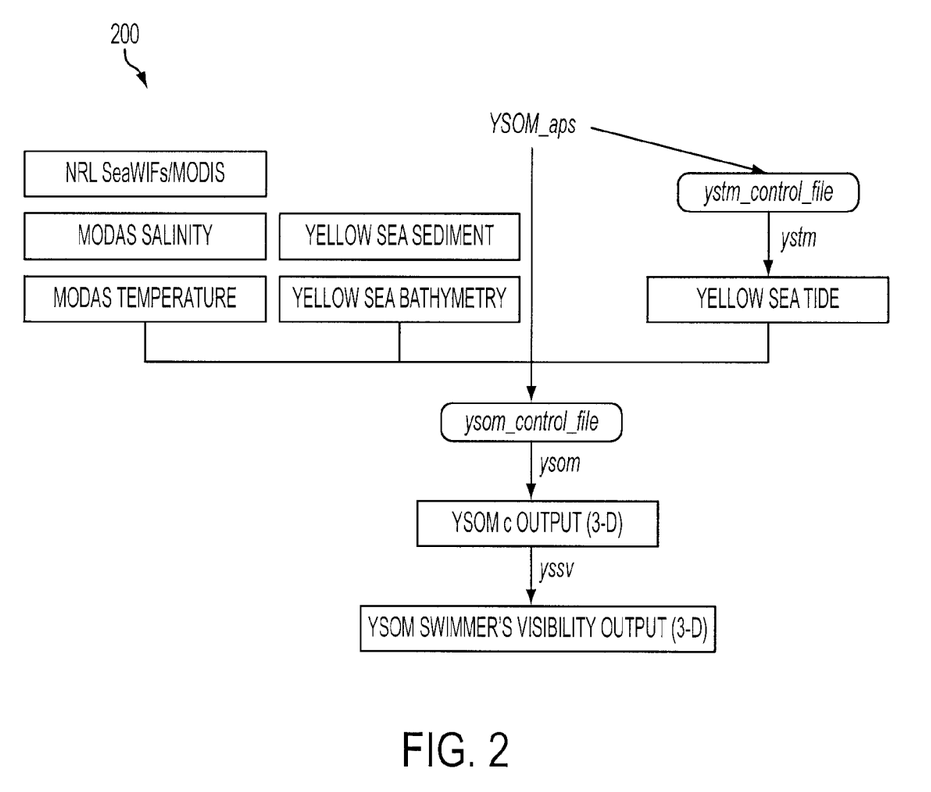
FIG. 2 illustrates schematically the architecture of a system of FIG. 1.
Figure 3:
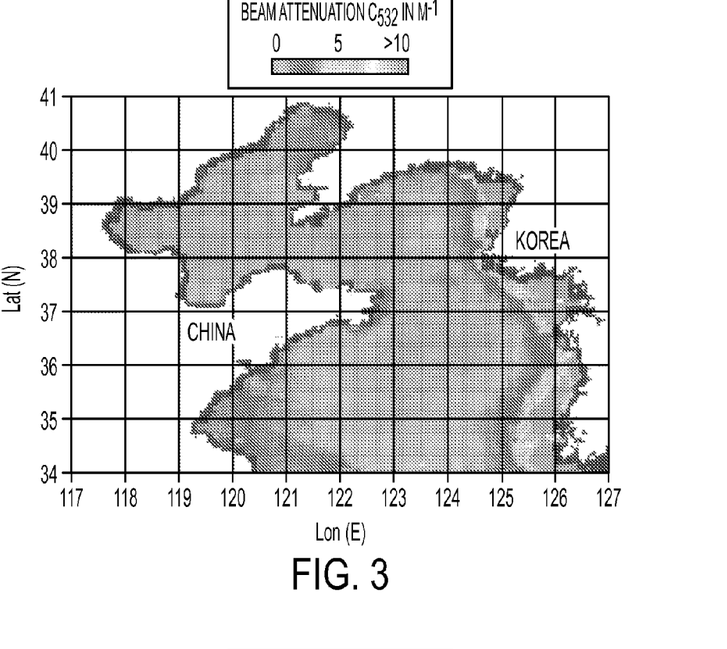
FIGS. 3 and 4 illustrates outputs of the system of FIG. 1.
Figure 4:
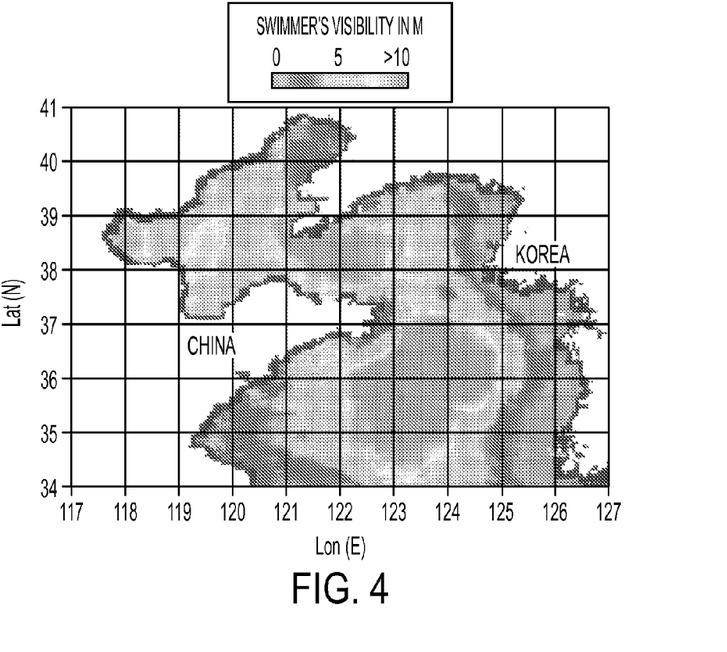

In an exemplary embodiment, the system 100 is used to estimate the spectral attenuation coefficient and swimmer's visibility from the surface to the bottom of the Yellow Sea, located between China and Korea. FIG. 2 illustrates schematically the architecture of the system. FIG. 3 and 4 illustrates outputs of the system, showing beam attenuation coefficient $C_{532}$ in units of 1/meters, and swimmer's visibility on the surface at 532 nm wavelength in units of meters.

Figure 5:
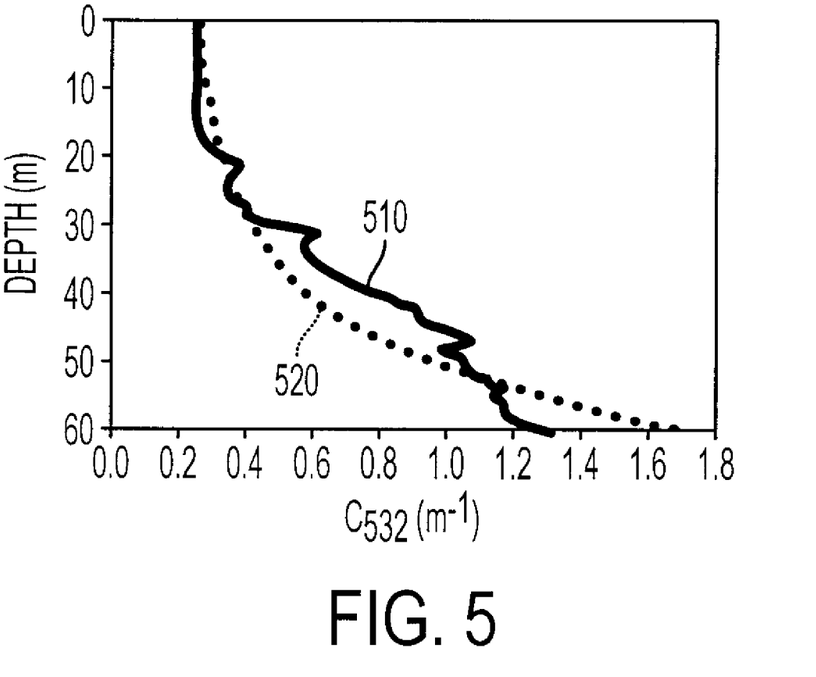
FIG. 5 compares the spectral attenuation results from a system in accordance with an embodiment of the invention with in-situ profiles obtained by oceanographic sampling.
Figure 6:
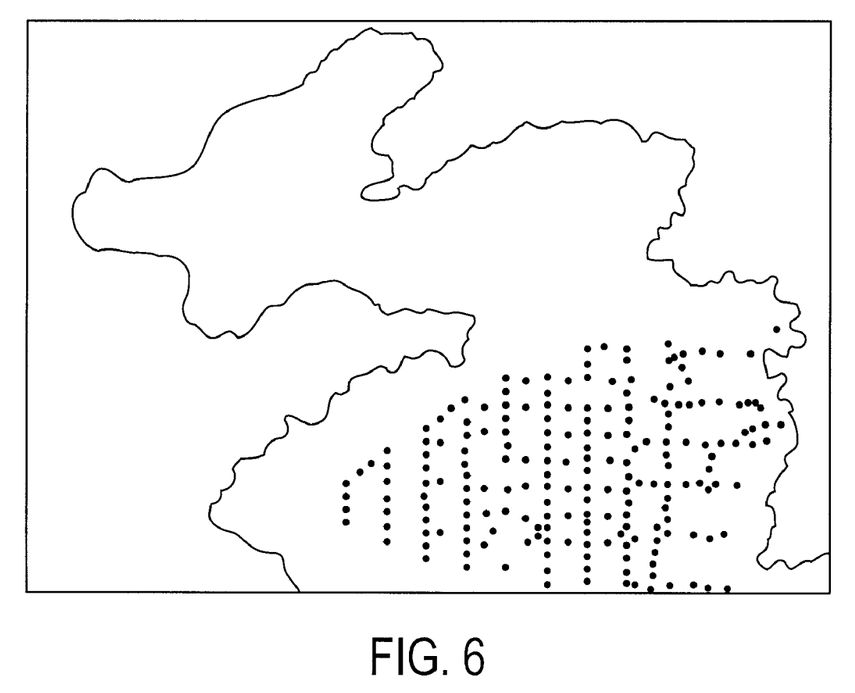
FIG. 6 is a map showing locations of situ measurements used for the training set and for evaluation for the results of FIG. 5.

FIG. 5 compares the results of the a system prediction for spectral attenuation in the Yellow Sea with in-situ profiles obtained by oceanographic sampling. The profile of spectral attenuation measurements 510 was taken at different depths in the water column starting at the surface and ending at the bottom at one specific location. The system 100 calculated the spectral attenuation estimates shown as the dotted curve 520. Locations of situ measurements used for the training set and for evaluation are shown in FIG. 6.

It is noted that while the default algorithm and clear sky algorithm described herein use 28 and 29 inputs, respectively, it is also possible to use fewer inputs, or a larger number of inputs, depending on the region being modeled and the availability of stations for which normalized water leaving irradiance has been measured. The default algorithm can be trained with different number of stations, for example, 36, 62, 108, 173, and 285 daytime and nighttime station data, or greater or lesser numbers of daytime and nighttime stations. The clear sky algorithm can be trained with 36, 62, 108, and 166 daytime stations, or greater or lesser numbers of daytime stations.

Figure 7:
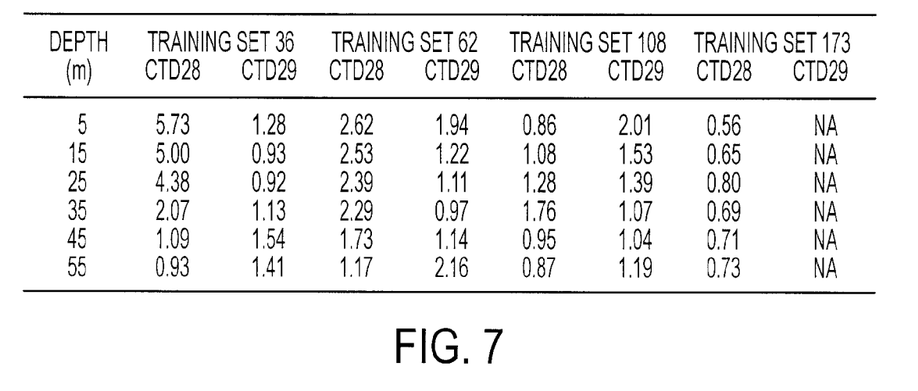
FIG. 7 illustrates the normalized root mean square error with respect to depth for the default algorithm and the clear sky algorithm with various numbers of training stations at depths.
Figure 8A:
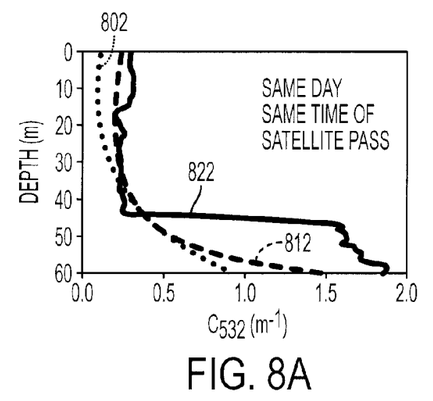
FIGS. 8A-8D are graphs illustrating the attenuation results of the system in accordance with an embodiment of the invention for predictions run with and without satellite data and for satellite data acquired at different times.
Figure 8B:
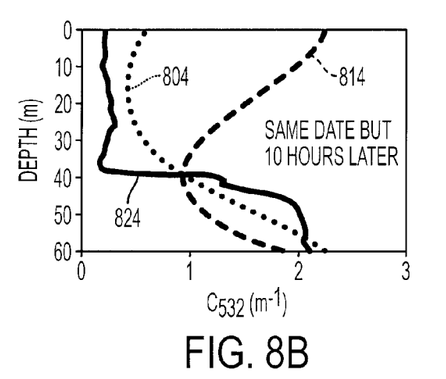
Figure 8C:
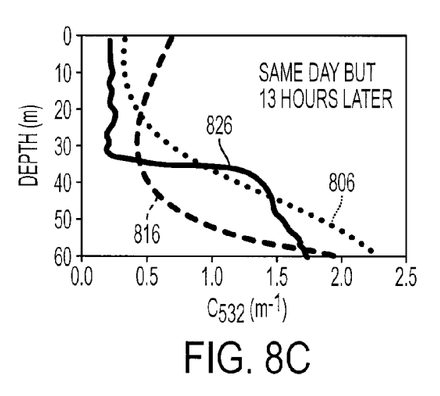
Figure 8D:
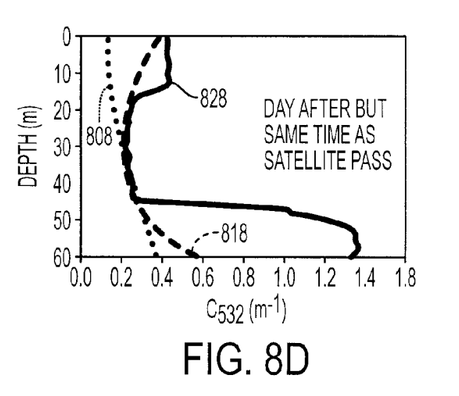

FIG. 7 illustrates the normalized root mean square error with respect to depth for the default algorithm and the clear sky algorithm with various numbers of training stations at depths.

As discussed in previous paragraphs, satellite data is preferably used for predictions only at times near when the time of the satellite imagery was acquired. FIG. 8A-8D illustrate the results for the attenuation for predictions run using the satellite data acquired on the same date and time, on the same date but 10 hours later, on the same date but 13 hours later, and on the day after but at the same time as the satellite pass. The dotted lines 802, 804, 806, and 808 show the results from the default algorithm. The dashed lines 812, 814, 816, and 818 show the results of the clear sky algorithm with normalized water leaving irradiance from the satellite at different times. The solid lines 822, 824, 826, and 828 show the measured profile for attenuation.

The exemplary embodiment of the system described herein does not address in-flow of fresh water from rivers, thin layers of unexpected organic materials, and complicated mid-column structures in open water that may be the result of eddies or rings. As a result, the system can underestimate the light field near the mouths of rivers. Satellite data can contribute to the accuracy of results particularly in open water and mouths of rivers.

Other embodiments of the invention are directed to methods of estimating spectral attenuation and visibility at depths for a gridded ocean region. The method can include selecting a region and grid resolution, the number of layers for use in the model. The method can also include training the neural network with training data sets of in-situ measurements and satellite data imagery. The method further includes receiving tidal coefficients, receiving bathymetry data, receiving sediment data, and receiving density data, either as density or as temperature and salinity.

Other embodiments of the invention are directed to methods and systems for receiving the attenuation coefficients and visibility results of the system 100, and for displaying or retransmitting the results in their original or modified format.

Other embodiments include computer software and computer programs, as well as computer systems and computer readable media having programs for implementing the methods discussed above. A computer system is generally applicable for the various embodiments described according to the present invention. The computer system can include a processor, a volatile memory, e.g., RAM, a keyboard, a pointing device, e.g., a mouse, a nonvolatile memory, e.g., ROM, hard disk, floppy disk, CD-ROM, and DVD, and a display device having a display screen. Memory can store program instructions that are executable by a processor to implement various embodiments of a method in accordance with the present invention. A communications device may also be connected to enable information exchange between the computer system and other devices.

It should be understood that the term "computer system" is intended to encompass any device having a processor that executes instructions from a memory medium. The memory medium preferably stores instructions (also known as a "software program") for implementing various embodiments of a method in accordance with the present invention. In various embodiments the one or more software programs are implemented in various ways, including procedure-based techniques, component-based techniques, and/or object-oriented techniques, among others. Specific examples include FORTRAN, XML, C++ objects, Java and Microsoft Foundation Classes (MFC).

Other embodiments of the invention include methods of receiving, displaying, further processing, making available for download, and/or transmitting the results generated by the equations, the system 200 and methods discussed herein. Other embodiments of the invention include computer systems and computer readable media having programs or applications for receiving, displaying, further processing, and transmitting the results or information derived from the results, as well as for making the results available for retrieval by other users. The results can be the attenuation and visibility results in tabular, graphical, time series, or other formats.

The invention has been described with reference to certain preferred embodiments. It will be understood, however, that the invention is not limited to the preferred embodiments discussed above, and that modification and variations are possible within the scope of the appended claims.

What is claimed as new and desired to be protected by Letters Patent of the United States is:

1. A method for predicting water optical properties at a plurality of water depths for a location, comprising:
   providing training data to a neural network, the training data representative of water measurements at the location;
   thereafter receiving inputs including data representative of density, tidal information, water depth, and sediment data;
   generating spectral attenuation coefficients or visibility at a wavelength at a plurality of depths; and
   generating a map of the spectral attenuation coefficients or visibility, displaying the spectral attenuation coefficients or visibility, or storing the spectral attenuation coefficients or visibility for further retrieval or processing.

2. The method according to claim 1, wherein the data representative of density is a density value.

3. The method according to claim 1, wherein the data representive of density is temperature and salinity.

4. The method according to claim 1, wherein the wavelength is 532 nanometers.

5. The method according to claim 1, wherein the tidal information is sea surface height and current velocity.

6. The method according to claim 1, wherein the training data includes measurements of water clarity and irradiance measurements from at least one satellite.

7. The method according to claim 1, wherein the training data is a set of data from a plurality of locations.

8. The method according to claim 1, further comprising: generating values for visibility at at least one depth at the location.

9. The method according to claim 1, further comprising: generating values for visibility at the plurality of depths at the location.

10. The method according to claim 1, further comprising receiving irradiance data from a satellite, and incorporating said irradiance data in said generating of said values of optical attenuation.

11. The method according to claim 10, wherein said generating comprises:
   generating a first set of values of optical attenuation using a first algorithm that does not receive irradiance data from the satellite; and
   generating a second set of values of optical attenuation using a second algorithm that does receive irradiance data from the satellite.

12. The method according to claim 11, wherein said generating a second set of values of optical attenuation is done only when cloud-free satellite images are available.

13. The method according to claim 11, wherein said training data are input to the first algorithm, and both the first and second algorithms are updated with results of training the first algorithm.

14. The method according to claim 1, wherein said plurality of depths extends from a water surface to an ocean bottom.

15. The method according to claim 1, wherein said plurality of depths extends to about 60 meters below a water surface.

16. The method according to claim 1, wherein said plurality of depths are between two and three meters apart.

17. The method according to claim 11, wherein said first and second algorithms use a gradient descent search to minimize mean squared error between desired output patterns and an output value of the neural network.

18. The method according to claim 1, wherein said generating includes generating values at a plurality of locations within a grid.

19. The method according to claim 18, wherein said grid has a resolution of about 0.5 degrees.

20. A method for predicting water optical properties at a plurality of water depths for a location, comprising:
   providing training data to a neural network, the training data representative of water measurements at the location;
   thereafter receiving inputs including data representative of density, tidal information, water depth, and sediment data;
   generating spectral attenuation coefficients or visibility at a wavelength at a plurality of depths and at a plurality of locations within a grid; and
   generating a map representation of the grid with said spectral attenuation coefficients or visibility shown on said map representation.

* * * * *